United States Patent [19]

Braden et al.

[11] Patent Number: 5,405,522
[45] Date of Patent: Apr. 11, 1995

[54] REFERENCE ELECTRODE AND METHOD OF MAKING THE SAME

[75] Inventors: Christoph Braden, Köln; Jacques Deprez, Frechen; Martina Gojowczik, Monheim, all of Germany

[73] Assignee: Mannesmann Aktiengesellschaft, Dusseldorf, Germany

[21] Appl. No.: 209,551

[22] Filed: Mar. 10, 1994

[51] Int. Cl.⁶ .............................................. G01N 27/30
[52] U.S. Cl. ........................ 204/435; 204/96; 204/412; 427/117; 427/126.5; 427/180; 427/190; 427/202; 427/203; 427/205; 427/402; 427/419.2; 427/421; 427/430.1
[58] Field of Search .............. 204/435, 412, 400, 431, 204/432, 96; 427/117, 126.5, 180, 190, 202, 203, 205, 402, 419.2, 421, 430.1

[56] References Cited

U.S. PATENT DOCUMENTS

| | | | |
|---|---|---|---|
| 3,458,421 | 7/1969 | Dahms | 204/435 |
| 3,462,353 | 8/1969 | Every et al. | 204/435 |
| 3,591,482 | 7/1971 | Neff et al. | 204/435 |
| 3,909,386 | 9/1975 | Oswin et al. | 204/153.1 |

*Primary Examiner*—T. Tung
*Attorney, Agent, or Firm*—Cohen, Pontani, Lieberman, Pavane

[57] ABSTRACT

A reference electrode for an electrochemical three-electrode sensor, including a shaft, a platinum electrode embedded in the shaft, a platinum oxide coat at least partially covering the platinum electrode, and a polyhydantoin coat completely covering the platinum oxide coat and any exposed surface of the electrode not coated with platinum oxide.

13 Claims, 1 Drawing Sheet

REFERENCE ELECTRODE AND METHOD OF MAKING THE SAME

BACKGROUND OF THE INVENTION

1. Field of the Invention

The invention is directed to a reference electrode for an electrochemical three-electrode sensor that is essentially made of a shaft with a platinum electrode embedded therein.

2. Description of the Prior Art

In most electrochemical three-electrode sensors, an air electrode is used as a reference system. This air electrode is realized in a simple manner and is also sufficiently stable for most applications. Such an air electrode is described, for example, in U.S. Pat. No. 3,909,386. However, its use is restricted to applications in which there is a sufficient partial pressure in oxygen. Furthermore, air reference electrodes also react to a number of other gases with fluctuations in potential resulting in a source of systematic error. Attempts have been made to overcome this source of systematic error by constructional measures, but experience has shown that it is difficult to eliminate these errors entirely.

SUMMARY OF THE INVENTION

Accordingly, it is an object of the present invention to provide a reference electrode that is independent of partial pressure in oxygen so as to improve electrochemical three-electrode sensors for measuring oxygen and for measuring gas in an oxygen-free atmosphere.

Proceeding from a reference electrode having a shaft with a platinum electrode embedded therein, the present invention accomplishes the above by coating the platinum electrode entirely or partially with platinum oxide ($PtO_2$) and completely coating the $PtO_2$ coat as well as the surface of the electrode not coated with $PtO_2$, if any, with polyhydantoin.

The $PtO_2$ coat advantageously already contains polyhydantoin as a bonding agent.

According to a preferred embodiment of the invention, the thickness of the $PtO_2$ coat is 50 $\mu$m to 500 $\mu$m, preferably 150 $\mu$m to 300 $\mu$m. The thickness of the polyhydantoin coat is advisably in the range of 100 $\mu$m to 700 $\mu$m, preferably in the range of 300 $\mu$m to 600 $\mu$m.

The inventive construction provides many advantages which include the following:

1. The polyhydantoin coating enables the production of $Pt/PtO_2$ reference electrodes with a potential of 950 mV SHS which remain stable over a long period of time.

2. The new reference system for electrochemical three-electrode sensors is not dependent on partial pressure in oxygen and is accordingly suitable for use in three-electrode oxygen measurement cells and for measuring gas components in an oxygen-free atmosphere.

3. In addition to mechanical stabilization, an optimal wetting of the reference electrode is also achieved by the polyhydantoin coating. A frequent source of systematic error lies in incomplete conversion of the gas to be measured at the work electrode and diffusion to the reference system causing fluctuations in potential therein which lead to erroneous measurement signals. Due to the complete wetting of the reference electrode ensured by the polyhydantoin coating, such errors are suppressed by an order of magnitude so that the reference system is practically insensitive to gas shorts in the measurement cell.

4. Furthermore, a reduced warm-up time (response time) is observed in the reference electrode, and the new reference electrodes can be produced at relatively low cost in terms of manufacturing technology and have only slight variation between units (high reproducibility).

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWING

The single figure schematically shows a reference electrode pursuant to the present invention.

DETAILED DESCRIPTION OF THE PREFERRED EMBODIMENTS

Figure 1:
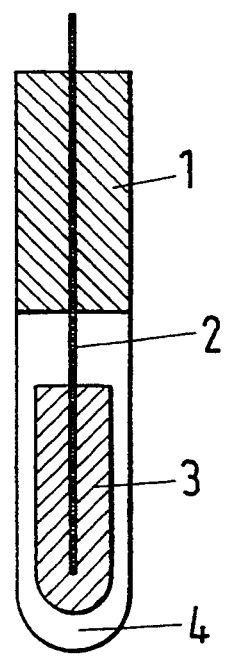

The reference electrode shown schematically in the drawing has a plastic shaft 1 in which a platinum electrode 2 in the form of a platinum wire or platinum plate is embedded. The free end of the platinum electrode 2 is enclosed along part of its length by a $PtO_2$ coat 3. The coating is effected electrochemically by electrodeposition or by mechanical compression of the $PtO_2$ powder onto the electrode, for example. However, such a $Pt/PtO_2$ reference system would not be sufficiently stable electrochemically or mechanically. The platinum electrode coated with $PrO_2$ is provided with an additional coating of polyhydantoin so as to achieve optimal wetting, mechanical fixing, and stabilization against dissolution of the $PtO_2$ coat when the reference electrode is immersed in the electrolyte. Polyhydantoin is a plastic lacquer which is produced by polyaddition of aromatic diisocyanates in 1,3-phenylene-bis(imino acetic acid ethyl ester) and is obtainable commercially. Polyhydantoin dissolves in aqueous solutions (swelling). However, a closed coating of polyhydantoin nevertheless remains impermeable for aqueous solutions. Due to this property, polyhydantoin has a conductivity of approximately 500 mS in contact with aqueous electrolytes, which is entirely sufficient for reference electrodes. The polyhydantoin coat 4 is applied by immersion or spraying. It also surrounds the portion of the platinum electrode 2 not coated with $PtO_2$. The thickness of the polyhydantoin coat 4 is 400 $\mu$m, for example. The application of the $PtO_2$ coat 3 can be facilitated by adding polyhydantoin to the $PtO_2$ powder as a bonding agent.

Due to their simple construction, such reference electrodes can be produced relatively simply and economically. The compact construction also enables its use in miniature measurement cells.

The invention is not limited by the embodiments described above which are presented as examples only but can be modified in various ways within the scope of protection defined by the appended patent claims.

We claim:

1. A reference electrode for an electrochemical three-electrode sensor, comprising: a shaft; a platinum electrode embedded in the shaft; a platinum oxide coat at least partially covering the platinum electrode; and a polyhydantoin coat completely covering the platinum oxide coat and any surface of the electrode not coated with platinum oxide.

2. A reference electrode according to claim 1, wherein the platinum oxide coat contains polyhydantoin as a bonding agent.

3. A reference electrode according to claim 1, wherein the platinum oxide coat has a thickness of 50 μm to 500 μm.

4. A reference electrode according to claim 3, wherein the platinum oxide coat has a thickness of 150 μm to 300 μm.

5. A reference electrode according to claim 1, where the polyhydantoin coat has a thickness of 100 μm to 700 μm.

6. A reference electrode according to claim 5, wherein the polyhydantoin coat has a thickness of 300 μm to 600 μm.

7. A reference electrode according to claim 1, wherein the shaft is made of plastic.

8. A reference electrode according to claim 1, wherein the platinum oxide coat completely covers the platinum electrode.

9. A method for producing a reference electrode for an electrochemical three-electrode sensor, comprising the steps of: providing a shaft; embedding a platinum electrode in the shaft; at least partially coating the platinum electrode with platinum oxide: and coating the platinum oxide coat and any exposed surface of the electrode not coated with platinum oxide with polyhydantoin.

10. A method as defined in claim 9, wherein the polyhydantoin coating steps includes spraying the polyhydantoin onto the platinum oxide coat and any exposed surface of the electrode.

11. A method as defined in claim 9, wherein the polyhydantoin coating step includes immersing the platinum electrode in polyhydantoin.

12. A method as defined in claim 9, wherein the platinum oxide coating step includes electrochemically depositing the platinum oxide on the electrode.

13. A method as defined in claim 9, wherein the platinum oxide coating step includes mechanically compressing platinum oxide powder on the electrode.

* * * * *